United States Patent
Muehlsteff

(10) Patent No.: US 10,213,114 B2
(45) Date of Patent: Feb. 26, 2019

(54) SYSTEM AND METHOD FOR BREATHING RATE MEASUREMENTS

(71) Applicant: KONINKLIJKE PHILIPS N.V., Eindhoven (NL)

(72) Inventor: Jens Muehlsteff, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 86 days.

(21) Appl. No.: 14/433,879

(22) PCT Filed: Oct. 3, 2013

(86) PCT No.: PCT/IB2013/059091
§ 371 (c)(1),
(2) Date: Apr. 7, 2015

(87) PCT Pub. No.: WO2014/057399
PCT Pub. Date: Apr. 17, 2014

(65) Prior Publication Data
US 2015/0250392 A1    Sep. 10, 2015

Related U.S. Application Data

(60) Provisional application No. 61/711,290, filed on Oct. 9, 2012.

(51) Int. Cl.
*A61B 5/0205* (2006.01)
*A61B 5/022* (2006.01)
(Continued)

(52) U.S. Cl.
CPC ............ *A61B 5/0205* (2013.01); *A61B 5/022* (2013.01); *A61B 5/0816* (2013.01);
(Continued)

(58) Field of Classification Search
CPC ............................ A61B 5/7278; A61B 5/0816
(Continued)

(56) References Cited

U.S. PATENT DOCUMENTS 3,527,197 A    9/1970    Ware et al.
4,729,381 A    3/1988    Harada et al.
(Continued)

FOREIGN PATENT DOCUMENTS

CN           102440780         5/2012
EP            2417908 A1       2/2012
(Continued)

OTHER PUBLICATIONS

Muehlsteff, J., et al.; The use of a two channel Doppler radar sensor for the characterization of heart motion phases; 2006; IEEE EMBS; 1:547-550.
(Continued)

*Primary Examiner* — Carl H Layno
*Assistant Examiner* — Dacheng Xie

(57) ABSTRACT

A device (100) for monitoring a subject's breathing rate is disclosed. A transducer (107) radiates energy towards the chest of a subject and receives the reflected energy. An analyzer (105) receives a signal corresponding to the reflected energy. The reflected energy would have undergone Doppler frequency shifts due to the motion of the chest of the subject due to breathing, with reference to the transducer. The analyzer (105) analyzes the signal to calculate the breathing rate by measuring at least one of a periodicity of the signal and a number of cycles per unit time of the signal. In a preferred embodiment the transducer (107) is disposed in or on a sphygmomanometer cuff to radiate energy towards the chest of the subject and receive the energy reflected by the chest of the subject.

14 Claims, 3 Drawing Sheets

(51) Int. Cl.
 *A61B 5/08* (2006.01)
 *A61B 5/00* (2006.01)
 *A61B 8/08* (2006.01)
(52) U.S. Cl.
 CPC .......... *A61B 5/6824* (2013.01); *A61B 5/7278* (2013.01); *A61B 8/08* (2013.01)
(58) Field of Classification Search
 USPC .................................................. 600/300–301
 See application file for complete search history.

(56) References Cited

U.S. PATENT DOCUMENTS

| | | | |
|---|---|---|---|
| 5,010,890 | A | 4/1991 | Pfohl et al. |
| 5,919,141 | A | 7/1999 | Money et al. |
| 8,398,558 | B2 | 3/2013 | Thijs et al. |
| 8,834,383 | B2 | 9/2014 | Muehlsteff et al. |
| 8,870,785 | B2 | 10/2014 | Muehlsteff et al. |
| 2006/0074283 | A1 | 4/2006 | Henderson et al. |
| 2006/0100530 | A1* | 5/2006 | Kliot .................... A61B 5/0002 600/483 |
| 2010/0152600 | A1* | 6/2010 | Droitcour ................ A61B 5/05 600/534 |
| 2010/0222687 | A1* | 9/2010 | Thijs .................. A61B 5/02438 600/508 |
| 2011/0054277 | A1 | 3/2011 | Pinter et al. |
| 2011/0112425 | A1* | 5/2011 | Muhlsteff ............ A61B 5/0507 600/534 |
| 2012/0197128 | A1 | 8/2012 | Palti |
| 2012/0302900 | A1 | 11/2012 | Yin et al. |
| 2013/0135137 | A1 | 5/2013 | Mulder et al. |
| 2013/0165800 | A1* | 6/2013 | Shimizu ................ A61B 5/022 600/485 |
| 2013/0172770 | A1 | 7/2013 | Muehlsteff |
| 2013/0172771 | A1 | 7/2013 | Muehlsteff |

FOREIGN PATENT DOCUMENTS

| | | |
|---|---|---|
| JP | 2003275207 | 9/2003 |
| JP | 2012157435 | 8/2012 |

OTHER PUBLICATIONS

Muehlsteff, J., et al.; A handheld device for simultaneous detection of electrical and mechanical cardio-vascular activities with synchronized ECG and CW-Doppler radar; 2007; IEEE EMBS; pp. 5759-5762.

Muehlsteff, J., et al.; Comparison of Respiration Rate Monitoring with a Low-cost Doppler-Radar Sensor and Inductive Thorax-Plethysmography; 2009; IFMBE Proc.; 25(7)768-771.

Thijs, J. A., et al.; A comparison of continuous wave Doppler radar to impedance cardiography for analysis of mechanical heart activity; 2005; IEEE EMBS; 4:3482-3485.

* cited by examiner

SYSTEM AND METHOD FOR BREATHING RATE MEASUREMENTS

CROSS REFERENCE TO RELATED APPLICATIONS

This application is a national filing of PCT application Serial No. PCT/IB2013/059091, filed Oct. 3, 2013, published as WO 2014/057399 A1 on Apr. 17, 2014, which claims the benefit of U.S. provisional application Ser. No. 61/711,290 filed Oct. 9, 2012, which is incorporated herein by reference.

FIELD OF THE INVENTION

This invention belongs to the field of measurement and monitoring of breathing rate of a human subject.

BACKGROUND OF THE INVENTION

A number of physiological parameters are measured to estimate the state of health of a person. In the case of a patient in a hospital and especially in an intensive care unit (ICU) physiological parameters are measured on a continuous basis to monitor variations in the state of health of the patient. This is done to ensure timely medical intervention in case of deterioration in the state of health, especially when the deterioration is likely to endanger life.

One of the important parameters measured is the breathing rate, also called the respiratory rate. The most commonly used method in low acuity settings is to observe the rise and fall of the patient's chest during breathing and counting the number of inhalation and exhalation cycles, timed with a clock. This is problematic when the patient has irregular or shallow breaths due to breathing distress.

Devices and methods to automatically measure the breathing rate are known in the field, using different types of transducers. Some of those methods are impedance plethysmography, capnography (mainly used in ICUs) and inductive thoracic plethysmography (Respiband™) in sleep studies (polysomnography). All these methods require the positioning of the sensor on the patient's body or elsewhere by a trained person.

The published patent application US20100222687, assigned to the same assignee as that of the present application discloses a method of using a plurality of Doppler radars disposed on the seat belt or integrated into the seat belt for monitoring vital body signs of a person seated in a seat of a motor vehicle. The disclosed method unobtrusively monitors vital body signs like heart rate and respiration rate of the person seated in the motor vehicle.

SUMMARY OF THE INVENTION

There exists a need for a device for and a method of measuring the breathing rate of a patient for overcoming or mitigating one or more of the problems in the state of the art.

Such a device may have the advantage that it may not need a skilled person to measure the breathing rate manually. Further, it may not need a skilled person to position a sensor proximate to the patient. Since the device measures the breathing rate, the data may be stored, or transmitted to a system for further processing or used along with the other measured parameters for making decisions or for issuing alarms.

Normally, patient monitors used in ICUs use a sphygmomanometer cuff to measure the subject's BP, among other things. Thus the disclosed method may offer the advantage that it makes it convenient to dispose the transducer in the cuff and once the cuff is worn by the subject, the measurement of the breathing rate of the subject is enabled without any additional positioning of a separate transducer.

BRIEF DESCRIPTION OF THE DRAWINGS

These and other aspects of the disclosed device and the disclosed method are described in detail with reference to the following figures, wherein.

DETAILED DESCRIPTION OF EMBODIMENTS

Figure 1:
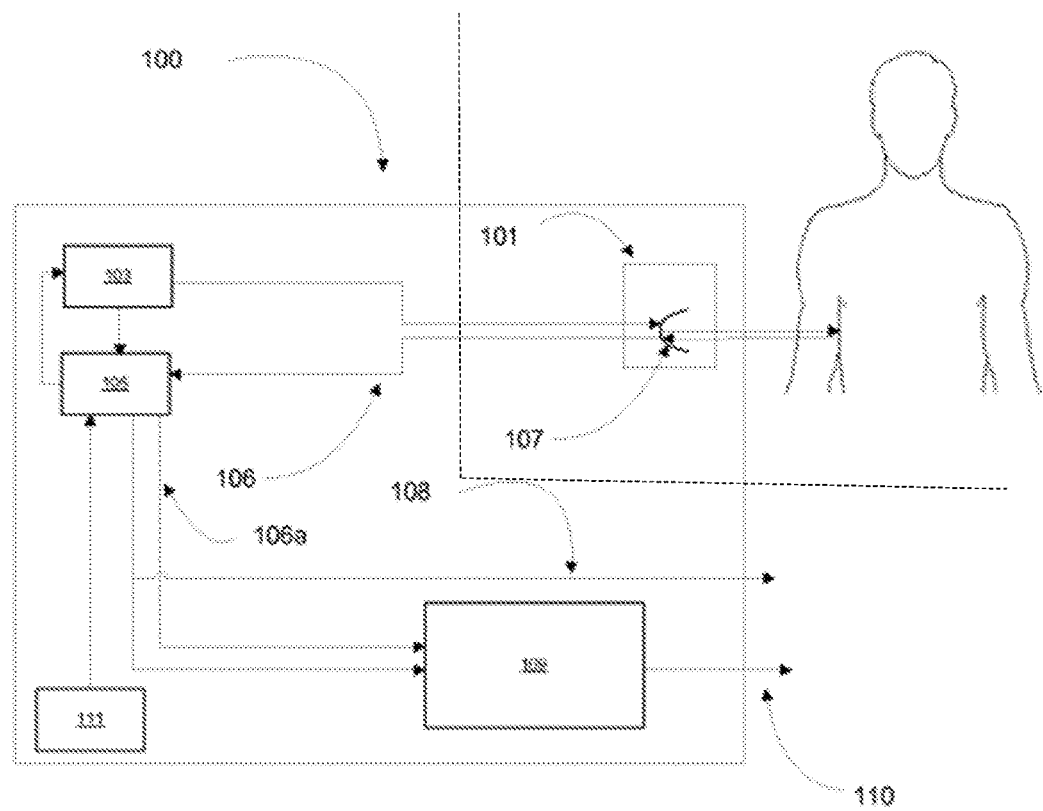
FIG. 1 is a schematic diagram of the disclosed device.

FIG. 1 is a schematic diagram of the disclosed device 100. A transducer 107 radiates energy towards the chest of a subject. The transducer 107 also receives the energy reflected by the chest of the subject. Since the chest of the subject is moving due to the subject's breathing the frequency of the reflected energy undergoes Doppler shift. The analyzer 105 receives a signal 106 (to be called transducer signal here after) corresponding to the reflected energy received by the transducer 107. The analyzer 105 analyzes the transducer signal 106 and determines the breathing rate of the subject.

To give a better picture of the device and its process, an oscillator 103 produces energy at a predetermined frequency and drives the transducer 107. The transducer is preferably an antenna that converts high frequency energy into corresponding electromagnetic radiation and vice versa or an ultrasound transducer that converts electrical energy into ultrasound energy of a predetermined frequency and vice versa. In the description hereafter only one of them, viz, electromagnetic waves, will be referred to for ease of description. It is to be understood that mutatis mutandis, the description applies to ultrasound waves also. However, if there are exceptions, the differences with reference to the two forms of energy will be stated at appropriate places.

With a stationary transducer, if the energy is reflected by a stationary object, there is no information in it to be demodulated. However in the present case the reflecting surface is the surface of the chest of the subject that moves in synchronism with the breathing of the subject, at least a part of the movement will be in a direction parallel to the direction of radiation. Thus the frequency of the reflected energy experiences Doppler shifts. The analyzer 105 may demodulate the transducer signal 106. The transducer signal 106 or demodulated signal 106a exhibits a complex dependency on the motion velocity, the motion amplitude and the distance between the chest and sensor. By using appropriate state-of-the-art signal processing, the subject's breathing rate can be obtained from the transducer signal 106 or demodulated signal 106a.

The analyzer 105 analyzes the signal to determine a pattern corresponding to a complete breathing cycle, in the demodulated signal 106a. It identifies at least the beginning and end of each complete cycle comprising one inhalation and one exhalation.

The analyzer 105 determines the time period for each cycle or a time period and amplitude of a pattern within each cycle or counts the number of complete cycles in a given period of time. The pattern within the cycle may correspond to the inhalation phase, exhalation phase and pauses, if any, between them. As is well known, to measure low frequencies the method of calculating the time period of each cycle is more accurate. The reciprocal of the period when multiplied by sixty yields the breathing rate of the subject in number of breaths per minute which is the most common unit for breathing rate. The breathing rate and other values determined by the analyzer 105 are outputted appropriately 108.

In one embodiment, analyzer 105 calculates the breathing rate by Fourier analysis of the transducer signal 106 or the demodulated transducer signal 106a. This may be advantageous for accurate measurements as the effect of noise could be eliminated or suppressed, eliminating the need for determining the start or end points of a cycle and thereby reducing or even eliminating the ambiguity therein.

In one embodiment, the device may output the demodulated signal 106a in a manner suitable for being displayed on a monitor 109. In another preferred embodiment, limiting values for the various measured values, such as breathing rate, or time for one breath (a complete cycle), time for each inhalation and each exhalation and so on may be input to the device through a suitable user interface 111 and whenever the individual values cross the limiting values, an indication or alarm 110 may be issued by the device. It is to be understood that the indication may be an audio or visual or audio-visual alarm. In one embodiment, the one or more outputs such as the breathing rate, the duration and amplitude of the phases of breathing, etc., may be outputted in a wired or wireless manner, to a central monitoring unit or a bedside unit or a central repository for storing a record of the monitored values or incidents when an alarm was issued.

Since breathing is a natural biological phenomenon, there may be large variations in the time per cycle between cycles. Thus, if the breathing rate calculated as described above is displayed as is, the display on the monitor 109 may change fairly rapidly and hence may be confusing or difficult to read. Thus, the output 108 may be a running average of a predetermined number of breathing cycles for the display unit to display. Alternatively, both the cycle by cycle breathing rate and the running average may be displayed. Once in a while, subjects take a longer breath than normal voluntarily or involuntarily. In one embodiment, when such events occur, such very long cycles may be dropped from the calculation of the average.

In one embodiment, the transducer 107 is disposed on a sphygmomanometer cuff 101 as shown in FIG. 1. The transducer may be releasably coupleable to the cuff, for example using hook-and-loop fasteners. Even though the cuff is shown at a distance from the upper arm of the diagrammatic representation of the subject, it is to be understood that the cuff 101 is wrapped or suitably placed on the upper arm of the subject, as prescribed. The transducer 107 is disposed on the cuff so that in use, when the cuff is worn by the subject as prescribed, the direction of radiation of the energy is substantially towards the chest of the subject. When the radiated energy encounters the chest of the subject, at least part of the energy is reflected by the chest and at least a part of the reflected energy is sensed by the transducer 107.

Figure 3:
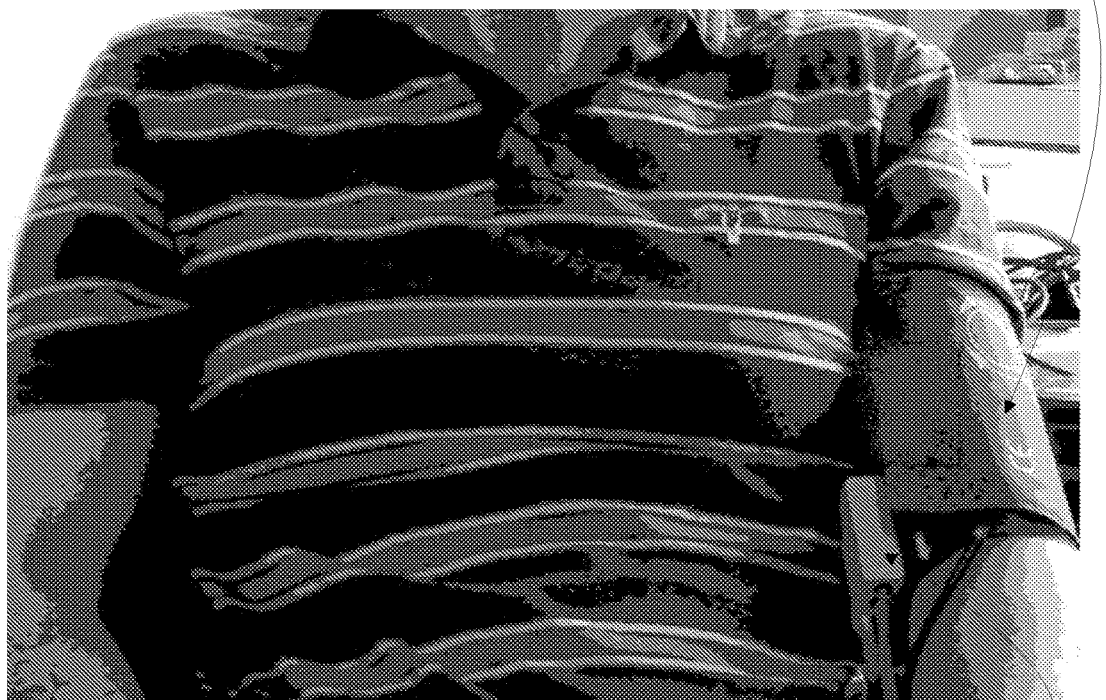
FIG. 3 is a representation of the disclosed device in use.

FIG. 3 shows the cuff 101, the transducer 107 disposed on the cuff 101 worn by a subject, as prescribed. In this embodiment, the breathing rate measurement device and a sphygmomanometer cuff based blood pressure measurement device may be two independent instruments. In one embodiment, the device according to claim 1 and the blood pressure measurement device are housed in the same enclosure. It may have a display that displays both the blood pressure and the breathing rate. In such a case, the antenna maybe advantageously disposed in the cuff, to be worn by the subject to be monitored so that no special care is needed in positioning the transducer in relation to the chest of the subject.

Figure 2:
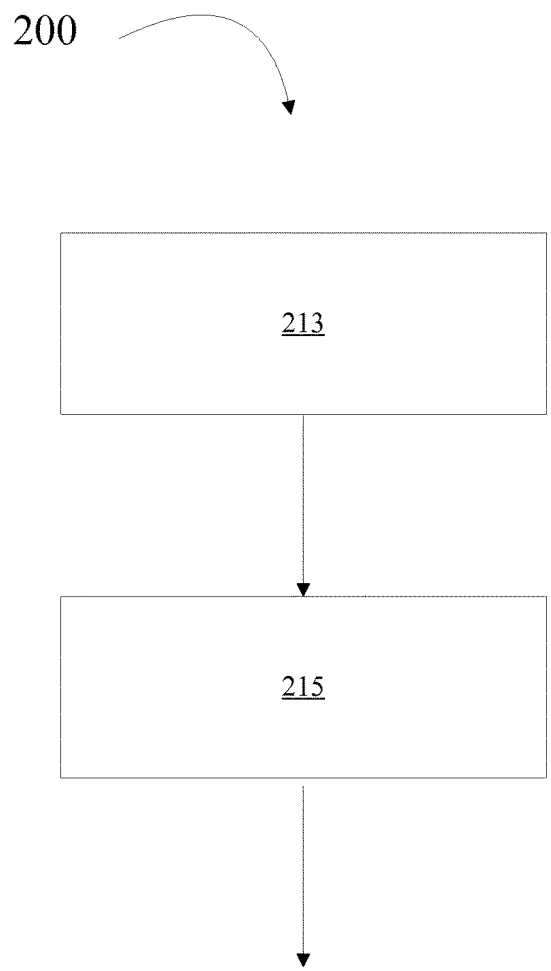
FIG. 2 is a diagrammatic representation of the disclosed method.

Now the disclosed method 200 is described in detail with reference to FIG. 2. The method comprises the steps as follows. In a disposing step 213, a transducer is disposed on the arm of the subject. In an analyzing step 215 the signal received from the transducer is analyzed to determine the breathing rate of the subject.

Since, when the subject breathes, the chest expands and contracts in synchronism with the breathing, the chest moves away from the transducer or towards it during exhalation and inhalation respectively. The movement produces shifts in the frequency of the radiated energy. The frequency shift, the Doppler shift, is negative frequency lower than the radiated frequency during exhalation and the shift is positive during inhalation. The magnitude of the shift is proportional to the rate of movement of the chest in relation to the transducer.

In an analyzing step 215, at least one temporal pattern in the signal is determined. This could mean that the part of the signal that represents the inhalation phase or exhalation phase and the pauses, if any, between them may be determined. At least complete cycles of breathing may be determined. This means that the start and end points of a complete breathing cycle may be determined. This could also mean that the starting points of two consecutive breathing cycles may be determined.

Alternatively the breathing rate could also be calculated by Fourier Analysis of the received signal. This may be advantageous for accurate measurements as the effect of noise could be eliminated more easily, reducing the ambiguity in determining the start or end of a cycle.

The time duration of the complete cycle determined is measured. The reciprocal of this measured time, when multiplied by sixty, yields the breathing rate in breaths per minute. Normally, higher frequencies are measured by counting the number of cycles in a certain period of time and the frequency in Hz is calculated. But for slow or long duration phenomenon, it is preferable to measure the time duration of each cycle and calculate the frequency in a suitable unit—Hz or cycles per minute, for instance.

The values measured or further values calculated based on those measurements are output suitably. The output could be displayed in the form of alphanumeric display, or with lights or audio-visual display and so on and combinations thereof and is not treated as a part of this description of the method.

The basic equations necessary to carry out the measurement using Doppler are explained below:

The Doppler signal for a single target, which is a good approximation of a subject's chest, is given by Equation 1 below as:

$$x(t) = a(t) \cdot \cos(\Theta(t))$$

where the amplitude a(t) can be assumed to be constant $a(t) = a_0$, since we consider only small distance changes (~cm) due to breathing and the beating heart, disregarding large subject movements. The phase-term in the equation above can be expressed by Equation 2 below as:

$$D(t) = \frac{4\pi}{\lambda} \left( \Xi + \sum_{k=1}^{4} \int_0^t v_k(t') dt' \right),$$

where λ is the wavelength of the transmitted waves, and Ξ is the sensor-chest distance for t=0. The sum consists of 4 terms due to the breathing motion (amplitude A of 5 mm-30 mm at 0.1 Hz-0.8 Hz), due to the beating heart (typically <5 mm at 0.5 Hz-3 Hz), the patient's global motion and—if applicable—movement of the sensor itself.

For an ideal measurement situation with breathing motion only and a perfect estimation of the phase term, equation (2) reduces to:

$$D(t) = \frac{4\pi}{\lambda}(\Xi + x(t))$$

wherein s(t) is the displacement of the chest beginning from t=0.

In one variant of the method the breathing rate displayed is the running average of a predetermined number of previous cycles. In one variant both the present breathing rate based on the latest full cycle and the running average as mentioned above are displayed together. In one variant the output includes an alarm when any of the measured or calculated parameters exceed or cross predetermined thresholds.

In one embodiment of the method, the transducer is disposed in a sphygmomanometer cuff. In one embodiment the transducer may be integrated into the cuff as an integral part. Since the cuff has a predefined position and orientation of application on the arm of the subject, the transducer may be so coupled or integrated into it, such that when the cuff is applied to the subject's arm properly, the transducer is in the appropriate position relative to the subject's chest for the measurement of the breathing rate.

The method has hitherto been described as a combination of the cuff based sphygmomanometer and the breathing rate. However it is to be understood that the method may be employed or practiced as an adjunct to or within a monitoring device or system which monitors various other parameters of a subject, for instance in an ICU or any other care facility. The parameters normally measured and monitored in that way are, but not limited to, blood pressure, Blood Oxygen Saturation (SpO2), heart rate and body temperature and so on.

In one embodiment, electromagnetic waves are used. Though other frequencies may be used, it is found that reliable results are obtained with a frequency of at least 1 GHz. Preferably, the frequency is between 20 GHz and 30 GHz and most preferably the frequency has a nominal value of 24 GHz. In another embodiment, ultrasound energy is employed with a frequency of at least 40 kHz. In other words the device and method may use the principle of Doppler RADAR or ultrasound based Doppler Sonar, also called Acoustic Doppler Sonar, using Ultrasound.

While the embodiments have been described in detail in the drawings and description, such drawings and description are to be considered exemplary and not restrictive; the invention is not limited to the disclosed embodiments. Wherever electrical connections or communication is referred to, it is to be understood that it could be effected in a wired or wireless manner. For instance, instead of displaying measured values of the duration of each phase of the breathing cycle, one or more of them may be displayed as a ratio of the duration of the phase and the duration of the whole breathing cycle and so on. Units described as distinct may in practice be realized in the same physical unit. The units may be built using any one or more devices of various technologies such as microcontrollers, microprocessors, digital signal processors (DSP's), programmable logic devices and so on. The distinction made here is for the ease of understanding and the implementation of the units and the practice of the steps may be varied by skilled persons to advantage.

Other variations to the disclosed embodiments can be understood and effected by those skilled in the art, in practicing the claimed invention, from a study of the drawings, the disclosure, and the appended claims. In the claims, the word "comprising" does not exclude elements or steps other than those mentioned, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

The invention claimed is:

1. A system for monitoring respiration of a subject, the device comprising:
   an oscillator configured to produce energy at a predetermined frequency;
   a transducer arranged to be worn on an upper portion of an arm of the subject and directed towards a chest of the subject, the transducer configured to:
      receive the produced energy from the oscillator;
      radiate energy towards the chest of the subject at the predetermined frequency;
      receive the energy reflected by the chest of the subject; and
      generate a signal indicative of a frequency of the received energy, the reflected energy undergoing a Doppler frequency shift based on motion of the chest; and
   an analyzer operatively coupled to the transducer, the analyzer being configured to:
      process the signal generated by the transducer; and
      determine a respiration rate of the subject in dependence on the Doppler frequency shifts in the reflected energy received by the transducer;
      wherein the oscillator and the analyzer are spaced from the transducer and the subject.

2. The system of claim 1 wherein the transducer comprises an ultrasound transducer or an antenna.

3. The system of claim 2, wherein the radiated energy has a frequency of approximately 24 GHz.

4. The system of claim 2, wherein the radiated energy is ultrasound energy with a frequency of at least 40 kHz.

5. The system of claim 1 further comprising a sphygmomanometer cuff configured to monitor a blood pressure of the subject, the cuff being mechanically coupleable to the transducer.

6. The system of claim 5 wherein the transducer is integrated into the sphygmomanometer cuff.

7. The system according to claim 5 wherein the analyzer is arranged for wireless communication with the transducer or the cuff or both to allow remote monitoring of the subject.

8. The system of claim 1, wherein the analyzer is further configured to:
   identify at least one breathing phase from the Doppler shift; and
   calculate at least one of a duration and an amplitude of the identified breathing phase.

9. The system of claim 1, wherein the analyzer is further configured to average at least one of a periodicity of respiration, a number of cycles of respiration per unit time, a duration of the phase, and an amplitude of the phase over at least one of a predetermined time period and a predetermined previous number of cycles.

10. The system of claim 9, wherein the analyzer is further configured to calculate a subsequent average value based on a current value within predetermined upper and lower limiting values or values that are within a predetermined multiple of a current average value.

11. The system of claim 10 wherein the analyzer is configured to compare at least one of the periodicity, the number of cycles per unit time, the duration of one or more phases and the amplitude of one or more phases with threshold values, and to generate an alarm signal.

12. The system of claim 1, further including:
a cuff configured to be worn on the arm of the subject, the transducer being mounted to the cuff; and
wherein the analyzer includes one or more processors operatively coupled to the transducer and configured to determine the respiration rate of the subject in dependence on the Doppler frequency shifts in reflected energy received by the transducer.

13. A method of monitoring the respiratory rate of a subject, the method comprising the steps of:
with an oscillator, producing energy at a predetermined frequency;
disposing a transducer on an upper portion of an arm of a subject and directed towards a chest of the subject;
with the transducer, receiver the produced energy from the oscillator;
with the transducer, radiating energy towards the chest of the subject;
with the transducer, receiving the energy reflected by the chest of the subject;
with the transducer, generating a signal indicative of a frequency of the received energy, the reflected energy undergoing a Doppler frequency shift based on motion of the chest
with an analyzer operatively coupled to the transducer, processing the signal generated by the transducer; and
with the analyzer, determine a respiration rate of the subject in dependence on Doppler frequency shifts in the reflected energy received by the transducer;
wherein the oscillator and the analyzer are spaced from the transducer and the subject.

14. The method of claim 13, wherein the disposing the transducer on the arm includes mechanically coupling to or integrating the transducer into a sphygmomanometer cuff.

* * * * *